US010646399B2

(12) United States Patent
Gordon

(10) Patent No.: US 10,646,399 B2
(45) Date of Patent: May 12, 2020

(54) METHODS FOR ENHANCING FEMALE ORGASM

(71) Applicant: Cliovana Ltd., Toronto (CA)

(72) Inventor: Robert Gordon, Toronto (CA)

(73) Assignee: Cliovana Ltd., Toronto, Ontario (CA)

( * ) Notice: Subject to any disclaimer, the term of this patent is extended or adjusted under 35 U.S.C. 154(b) by 0 days.

(21) Appl. No.: 16/137,813

(22) Filed: Sep. 21, 2018

(65) Prior Publication Data

US 2019/0343714 A1 Nov. 14, 2019

Related U.S. Application Data

(60) Provisional application No. 62/670,250, filed on May 11, 2018.

(51) Int. Cl.

| | |
|---|---|
| ***A61F 5/00*** | (2006.01) |
| ***A61H 19/00*** | (2006.01) |
| ***A61H 9/00*** | (2006.01) |
| ***A61H 23/02*** | (2006.01) |

(52) U.S. Cl.
CPC ........... *A61H 19/34* (2013.01); *A61H 9/0057* (2013.01); *A61H 23/0245* (2013.01); *A61H 2201/5007* (2013.01); *A61H 2201/5038* (2013.01)

(58) Field of Classification Search
CPC ........ A61H 19/00; A61H 19/30; A61H 19/34; A61H 9/0057; A61H 23/0245
USPC ........................................................... 600/38
See application file for complete search history.

(56) References Cited

U.S. PATENT DOCUMENTS

| | | | |
|---|---|---|---|
| 5,222,484 A | 6/1993 | Krauss et al. |
| 5,693,002 A | 12/1997 | Tucker et al. |
| 6,068,596 A | 5/2000 | Weth et al. |
| 6,368,292 B1 | 4/2002 | Ogden et al. |
| 7,390,308 B2 | 6/2008 | Schultheiss |
| 7,470,240 B2 | 12/2008 | Schultheiss et al. |
| 7,497,834 B2 | 3/2009 | Schaden et al. |
| 7,497,835 B2 | 3/2009 | Schultheiss et al. |
| 7,497,836 B2 | 3/2009 | Schultheiss et al. |
| 7,507,213 B2 | 3/2009 | Schultheiss et al. |
| 7,544,171 B2 | 6/2009 | Schaden et al. |
| 7,578,796 B2 | 8/2009 | Schultheiss et al. |
| 7,594,930 B2 | 9/2009 | Warlick et al. |

(Continued)

FOREIGN PATENT DOCUMENTS

| | | |
|---|---|---|
| CN | 104470485 A | 3/2015 |
| EP | 3192485 A1 | 7/2017 |

(Continued)

OTHER PUBLICATIONS

"New Generation of Shockwave Devices with the Controls in the Handpiece", Shockwave Canada Inc., brochure, Oct. 30, 2014, pp. 1-12.

(Continued)

*Primary Examiner* — John P Lacyk
(74) *Attorney, Agent, or Firm* — Bereskin & Parr LLP/S.E.N.C.R.L., s.r.l.; Tony Orsi

(57) ABSTRACT

Methods and devices are described for performing at least one of enhancing female sexual arousal, enhancing female sexual pleasure, or enhancing an ability to achieve or experience a more pleasurable orgasm for a female. In some cases, an acoustic wave stimulus is combined with one or more of providing a suction stimulus and a vibration stimulus as this may be further beneficial to the female.

18 Claims, 4 Drawing Sheets

(56) References Cited

U.S. PATENT DOCUMENTS

| | | | |
|---|---|---|---|
| 7,600,343 | B2 | 10/2009 | Schultheiss et al. |
| 7,601,127 | B2 | 10/2009 | Schultheiss et al. |
| 7,695,443 | B2 | 4/2010 | Voss |
| 7,775,995 | B2 | 8/2010 | Voss |
| 7,841,995 | B2 | 11/2010 | Schultheiss et al. |
| 7,883,482 | B2 | 2/2011 | Schultheiss et al. |
| 7,905,845 | B2 | 3/2011 | Schultheiss et al. |
| 7,967,740 | B2 | 6/2011 | Mertens et al. |
| 7,988,648 | B2 | 8/2011 | Warlick et al. |
| 8,057,411 | B2 | 11/2011 | Warlick et al. |
| 8,162,859 | B2 | 4/2012 | Schultheiss et al. |
| 8,257,282 | B2 | 9/2012 | Uebelacker et al. |
| 8,529,451 | B2 | 9/2013 | Warlick et al. |
| 8,535,249 | B2 | 9/2013 | Uebelacker et al. |
| 8,778,414 | B2 | 7/2014 | Warlick |
| 9,011,316 | B2 | 4/2015 | Mertens et al. |
| 9,060,525 | B2 | 6/2015 | Warlick |
| 2012/0215142 | A1 | 8/2012 | Spector et al. |
| 2012/0239055 | A1 | 9/2012 | Spector et al. |
| 2015/0141880 | A1 | 5/2015 | Ehrenreich |
| 2015/0224345 | A1 | 8/2015 | Warlick |
| 2016/0074276 | A1 | 3/2016 | Scheuring et al. |
| 2016/0143802 | A1 | 5/2016 | Tranfaglia et al. |
| 2017/0202731 | A1 | 7/2017 | Goldfarb et al. |
| 2017/0209708 | A1 | 7/2017 | Schwarz |
| 2017/0266076 | A1 | 9/2017 | Chen |
| 2017/0296427 | A1 | 10/2017 | Warlick et al. |
| 2018/0049943 | A1 | 2/2018 | Warlick |
| 2018/0147111 | A1 | 5/2018 | Gaines |

FOREIGN PATENT DOCUMENTS

| | | | |
|---|---|---|---|
| WO | 2007/098300 | A2 | 8/2007 |
| WO | 2017/066625 | A1 | 4/2017 |

OTHER PUBLICATIONS

Prouza, "Shockwave therapy in musculoskeletal treatment", BTL, PowerPoint presentation, pp. 1-55, accessed on May 2, 2018.

"Treatment with VACU-ACTOR Technology", STORZ Medical, Quick Reference Guide, Shockwave Canada Inc., accessed on Dec. 2017, pp. 1 and 2.

Novak et al., "Radial ESWT Update: New Observations to Explain Positive Treatment Results in Sports Medicine", Lohrer eds., in Shock Waves in Sports Medicine, vol. 8, Level 10 Buchverlag, Germany, Mar. 26, 2018, pp. 127-157.

"Shockwave Theory", Extracorporeal Shockwave Therapy Education, web page, accessed on May 2, 2018, <http://www.shockwavetherapy.education/index.php/theory/types-of-shockwave>.

Berman et al., "Female sexual dysfunction", Urologic Clinics, May 2001, 28(2): 405-416.

Meston et al., "Disorders of orgasm in women", The Journal of Sexual Medicine, Jul. 2004, 1(1): 66-68.

Doctors Studio, web site accessed on May 17, 2018, <https://www.doctorsstudio.com/women/shock-wave-therapy-for-women>.

"Cupping Therapy", WebMD Medical Reference, Aug. 10, 2016, <https://www.webmd.com/balance/guide/cupping-therapy#1>.

Rullo et al., "Genital vibration for sexual function and enhancement: best practice recommendations for choosing and safely using a vibrator", Taylor & Francis Online, web article, Jan. 4, 2018, <http://www.tandfonline.com/doi/abs/10.1080/14681994.2017.1419558>.

"Geneveve by Viveve—a unique women's health and wellness treatment", Viveve, accessed on Mar. 14, 2018 <www.viveve.com/geneveve-treatment>.

"MASTERPULS "Ultra" MP200", Shockwave Canada Inc., web page accessed on Apr. 26, 2018, <https://shockwavecanadainc.ca/products/mp200>.

"How Shockwave Therapy Really Works", Shockwave Canada Inc., web page accessed on Mar. 14, 2018 <https://shockwavecanadainc.ca/science/about-shockwave-therapy>.

"Shock Wave Therapy for Erectile Dysfunction", New Jersey Urology , web article, Jan. 15, 2018.

Borreli, "Intensify Your Sex Play: 'Electrosex' Uses Electrical Currents to Stimulate Nerve Endings in Erogenous Zones", web article, accessed on Mar. 14, 2018.

"The Erotic Effects of Cupping", Black Rabbit, web article, Aug. 22, 2011, <http://blackrabbit.com.au/blog/the-erotic-effects-of-cupping>.

Lin, "Vacuum-cupping Massage for more sexual orgasm!", Research Center for Multiple, Sexual Orgasms, web page, accessed on Mar. 14, 2018, <http://www.actionlove.com/cases/case8538.htm>.

Lin, "Vacuum-cupping massage for sexual orgasm and erectile dysfunction!", Research Center for Multiple, Sexual Orgasms, web page accessed on Mar. 14, 2018, <http://www.actionlove.com/msg.htm>.

"Dermotonus Slim Vacuum Therapy Unit", 3B Scientific, web page accessed on May 4, 2018, <https://www.a3bs.com/dermotonus-slim-vacuum-therapy-unit-w78005-ibramed-d-91,p_1210_26560.html>.

"What Is GAINSWave?", web page accessed on Mar. 14, 2018 <https://joingainswave.com/what-is-gainswave>.

Femiwave, "A Breakthrough Solution for Women's Sexual Health", website, Apr. 2018, 29 pages <https://femiwave.com>.

Examiner's Report dated Jan. 9, 2019 issued in corresponding CA Patent Application No. 3,018,262, pp. 1-5.

Qureshi et al., "History of cupping (Hijama): a narrative review of literature", Journal of Integrative Medicine, 2017, 15(3): 172-181.

Bayer AG et al., "FSFI", website, 2000, 1 page <http://www.fsfiquestionnaire.com>.

Chung, "Evaluation of clinical efficacy, safety and patient satisfaction rate after low-intensity extracorporeal shockwave therapy for the treatment of male erectile dysfunction: an Australian first open-label single-arm prospective clinical trial", BJU International, 2015, 115 Suppl 5: 46-49.

Herbenick et al., "Women's Experiences With Genital Touching, Sexual Pleasure, and Orgasm: Results From a U.S. Probability Sample of Women Ages 18 to 94", Journal of Sex and Marital Therapy, Feb. 2018, 44(2): 201-212. [posted online: Jul. 5, 2015; accepted manuscript pp. 1-35].

Murata et al., "Extracorporeal shockwaves induce the expression of ATF3 and GAP-43 in rat dorsal root ganglion neurons", Autonomic Neuroscience: Basic and Clinical, 2006, 128(1-2): 96-100.

Wang et al., "Shock wave therapy induces neovascularization at the tendon-bone junction: A study in rabbits", Journal of Orthopaedic Research, 2003, 21(6): 984-989.

Lee et al., "Effects of extracorporeal shock wave therapy on functional recovery and neurotrophin-3 expression in the spinal cord after crushed sciatic nerve injury in rats", Ultrasound Med Biol., 2015, 41(3): 790-796.

Hausner et al., "Improved rate of peripheral nerve regeneration induced by extracorporeal shock wave treatment in the rat", Experimental Neurology, 2012, 236: 363-370.

Extended European Search Report dated Apr. 4, 2019 in corresponding EP Patent Application No. 18195979.2.

Examiner's Report dated May 23, 2019 in corresponding CA Patent Application No. 3,018,262.

Examiner's Report and Search Report dated Sep. 20, 2019 in corresponding CA Patent Application No. 3,018,262 (4 pages).

"Medica 2016: Storz Medical demonstrates its leading role in the field of shock wave therapy", made public on Dec. 5, 2016 <https://www.karlstorzlitho.com/news/entry/medica-2016-storz-medical-demonstrates-its-leading-role-in-the-field-of-shock-wave-therapy.html> (4 pages).

"Shock Waves", The Physics Hypertextbook, 1998, last accessed in 2019 <https://physics.info/shock> (3 pages).

"Acoustic wave", Wikipedia, 2006, last accessed in 2019 <https://en.wikipedia.org/wiki/Acoustic_wave> (6 pages).

Ogden et al., "Principles of Shock Wave Therapy", Clinical Orthopaedics and Related Research (2001), 387: 8-17.

"Sound", Wikipedia, 2001, last accessed in 2019 <https://en.wikipedia.org/wiki/Sound#Sound_wave_properties_and_characteristics>(11 pages).

(56) References Cited

OTHER PUBLICATIONS

"Massage Therapy Styles and Health Benefits", WebMD, 2016, reviewed by Melinda Ratini on Oct. 2, 2018 <https://www.webmd.com/balance/guide/massage-therapy-styles-and-health-benefits#1> (4 pages).

Examinees Report and Search Report dated Mar. 9, 2020 in corresponding CA Patent Application No. 3,018,262 (11 pages).

"Extracorporeal shock wave therapy (ESWT) in orthopedics", made public by Storz in "Arthroscopy and Sports Medicine, 5th Edition" in Feb. 2017, pp. 236-237 <https://www.karlstorz.com/cps/rde/xbcr/karlstorz_assets/ASSETS/3343831.pdf>.

METHODS FOR ENHANCING FEMALE ORGASM

CROSS-REFERENCE

This application claims the benefit of U.S. Provisional Patent Application No. 62/670,250, filed May 11, 2018, and the entire content of U.S. Provisional Patent Application No. 62/670,250 is hereby incorporated by reference.

FIELD

The various embodiments described herein relate to methods for enhancing female sexual response, and more particularly relate to methods involving the use of different types of stimuli for enhancing or improving female orgasm and female sexual arousal.

BACKGROUND

Females may have trouble getting sexually aroused, experiencing sexual pleasure and achieving an orgasm during sex. This may be due to several different reasons such as, but not limited to, sexual arousal disorder, female orgasmic disorder, and female sexual pain disorder. Sometimes these issues may be due to an underlying physiological or psychological problem. Conditions affecting female sexual function occur in about 30-50% of women in the United States (Berman, 2001), with 24% of American women reporting trouble enjoying or achieving an orgasm (Meston, 2004). Accordingly, this affects millions of women.

Over the years, there have been many attempts at helping women achieve and enjoy sexual arousal and orgasm. One of these attempts involves vaginoplasty procedures. However, these procedures are often painful and carry significant risk, and have achieved various mixed results. Likewise, clitoral injection procedures focused on enhancing female orgasm by increasing the sensitivity of the clitoris have also achieved mixed results.

SUMMARY

The following is provided to introduce the reader to the more detailed discussion to follow and it is not intended to limit or define any claimed or as yet unclaimed subject matter. One or more groups of claimed or unclaimed subject matter may reside in a combination or a sub-combination of the elements or process steps as described in any part of this document including its claims and figures.

In one broad aspect, in at least one embodiment described herein, there is provided a method for performing at least one of enhancing female sexual arousal, enhancing female sexual pleasure, and/or enhancing an ability to achieve or experience a more pleasurable orgasm for a female, wherein the method comprises: setting values for stimulus parameters; applying an acoustic stimulus at a perineum of the female; and applying at least one of a suction stimulus and a vibrational stimulus to the perineum of the female, wherein the stimuli are applied in the same session.

In at least some embodiments, the method comprises applying the suction stimulus before applying the acoustic stimulus.

In at least some embodiments, the method comprises applying the vibration stimulus after applying the acoustic stimulus.

In at least some embodiments, the method comprises applying the acoustic stimulus to at least one of a clitoral region and a perineal region of the perineum in any order.

In at least some embodiments, the method comprises applying at least one of about 500 to 2000 acoustic pulses to the clitoral region and about 500 to 2000 acoustic pulses to the perineal region.

In at least some embodiments, the method comprises applying the acoustic stimulus with an intensity of about 0.1 to 0.25 mJ/mm$^2$.

In at least some embodiments, the method comprises applying the acoustic stimulus at a frequency of about 4 to 15 Hz.

In the embodiments, the acoustic stimulus typically comprises one of low energy shockwaves, pressure pulses, acoustic waves, or radial shockwaves.

In at least some embodiments, the method comprises applying the acoustic stimulus for about 2 to 4 minutes.

In at least some embodiments, the method comprises applying the suction stimulus to a clitoral region of the perineum with an intensity of about 1 to 5 bars when a MASTERPULS® "ULTRA" MP200 device is used and a VACU-ACTOR® accessory is the suction probe.

In at least some embodiments, the method comprises applying the suction stimulus for about 1 to 4 minutes.

In at least some embodiments, the method comprises applying the vibration stimulus to a clitoral region of the perineum with an intensity of about 1.6 to 2.8 bars when a MASTERPULS® "ULTRA" MP200 device is used and a V-ACTOR® accessory is the vibration probe.

In at least some embodiments, the method comprises applying the vibration stimulus with a frequency of about 21 Hz.

In at least some embodiments, the method comprises applying the vibration stimulus for about 30 seconds to 1 minute.

In at least some embodiments, the method is performed on the patient two to three times per week at an interval of two to three days.

In another broad aspect, in at least one embodiment described herein, there is provided a use of a device for performing at least one of enhancing female sexual arousal, enhancing female sexual pleasure, and/or enhancing an ability to achieve or experience a more pleasurable orgasm for a female, wherein the device comprises: a user interface that is configured to set values for stimulus parameters; an acoustic unit that is configured to provide an acoustic stimulus at the perineum of the female; and at least one of: a suction unit that is configured to provide a suction stimulus to the perineum of the female, and a vibration unit that is configured to provide a vibration stimulus to the perineum.

In at least some of the use embodiments, the acoustic unit is configured to provide the acoustic stimulus with an intensity in a range of about 1.0 to 3.6 bars for about 2 to 3 minutes when the device is the MASTERPULS® "ULTRA" MP200 and a V-ACTOR® accessory is the vibration probe.

In at least some of the use embodiments, the acoustic unit comprises an acoustic probe that is configured to apply the acoustic stimulus to at least one of a clitoral region and a perineal region of the perineum.

In at least some of the use embodiments, the suction unit is configured to provide the suction stimulus with an intensity in a range of about 1.0 to 5.0 bars for about 1 to 4 minutes when the device is the MASTERPULS® "ULTRA" MP200 and the V-ACTOR® accessory is the vibration probe.

In at least some of the use embodiments, the vibration unit is configured to provide the vibration stimulus with an intensity in a range of about 1.6 to 2.8 bars for about 30 seconds to 1 minute when the device is the MASTER-PULS® "ULTRA" MP200 and the V-ACTOR® accessory is the vibration probe.

In at least some of the use embodiments, the vibration unit comprises a vibration probe that is configured to apply the vibration stimulus to a clitoral region of the perineum.

In at least some of the use embodiments, the use comprises using the suction unit to provide the suction stimulus and then using the acoustic unit to apply the acoustic stimulus.

In at least some of the use embodiments, the use comprises using the vibration unit to provide the vibration stimulus after using the acoustic unit to apply the acoustic stimulus.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

DRAWINGS

For a better understanding of the various embodiments described herein, and to show more clearly how these various embodiments may be carried into effect, reference will be made, by way of example, to the accompanying drawings which show at least one example embodiment and the figures will now be briefly described.

Figure 1:
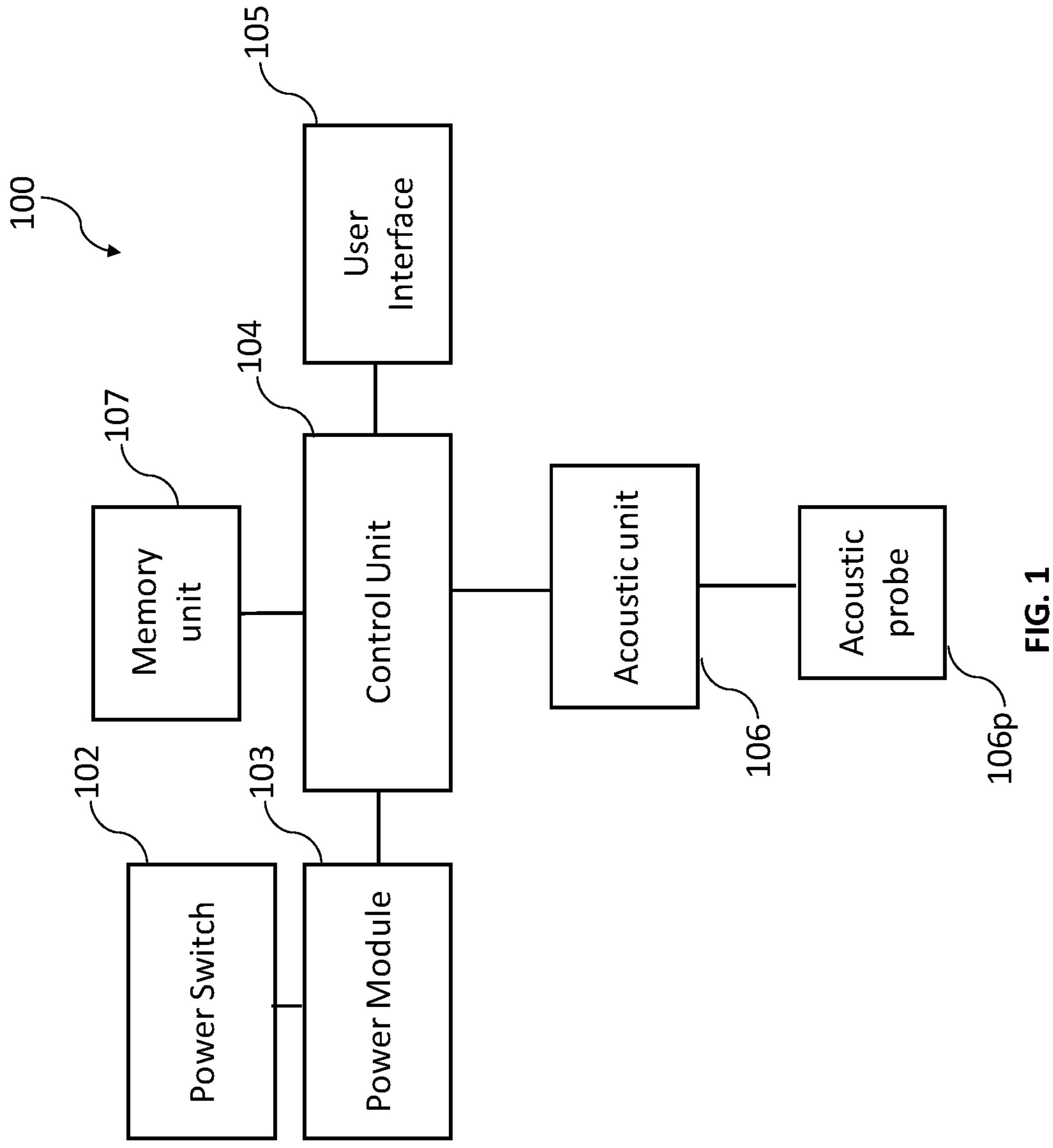
FIG. 1 is a block diagram of an example embodiment of a device capable of producing acoustic stimuli that may be used to perform one or more of the various methods described in accordance with the teachings herein.

Further aspects and features of the embodiments described herein will appear from the following description taken together with the accompanying drawings.

DESCRIPTION OF VARIOUS EMBODIMENTS

Various apparatuses or processes will be described below to provide an example of at least one embodiment of claimed subject matter. No embodiment described below limits any claimed subject matter and any claimed subject matter may cover processes, apparatuses, devices, or systems that differ from those described below. The claimed subject matter is not limited to apparatuses, devices, systems, or processes having all of the features of any one apparatus, device, system, or process described below or to features common to multiple or all of the apparatuses, devices, systems, or processes described below. It is possible that an apparatus, device, system, or process described below is not an embodiment of any claimed subject matter. Any subject matter that is disclosed in an apparatus, device, system, or process described below that is not claimed in this document may be the subject matter of another protective instrument, for example, a continuing patent application, and the applicants, inventors, or owners do not intend to abandon, disclaim, or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the end result is not significantly changed. These terms of degree should be construed as including a deviation of the modified term such as 1%, 2%, 5% or 10%, for example, if this deviation does not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made such as 1%, 2%, 5% or 10%, for example, if the end result is not significantly changed.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

As used herein, the term "acoustic stimulus" means a stimulus comprising a low energy shockwave, a pressure pulse, a focused shockwave, or a radial shockwave. In general, a shockwave is a transient acoustic wave.

As used herein, the term "low energy shockwave" is an acoustic wave that has a low amount of energy such as less than about 0.08 mJ/mm$^2$, for example. A low energy shockwave may comprise a longer sinusoidal waveform in comparison to a focused shockwave (i.e. a high energy shockwave).

As used herein, the term "focused shockwave: is an acoustic wave that has a higher amount of energy such as more than about 0.28 mJ/mm$^2$, for example. A focused shockwave can cause fragmentation and breakdown solid bodies. A focused shockwave can be caused by spark discharge, piezoelectric or electromagnetic means.

As used herein, the term "radial shockwave" means a non-focused wave generated by either air compression or electromagnetism. Radial waves are slower, have less wave energy, and are more sinusoidal in appearance than focused waves.

As used herein, the term "pressure pulse", which may also be referred to as a pressure wave, means acoustic energy that has an intensity of about 1 to 5 mJ/mm$^2$. It should be noted that a pressure wave is different from a shockwave in that pressure waves have a slower rise time, less energy (and therefore causes less pressure to the target region to which it is applied) and has different waveforms than a shockwave.

As used herein, the unit "mJ/mm$^2$" means millijoules per millimetre squared.

The inventor has discovered that different types and combinations of stimuli can be used to enhance female arousal, sexual pleasure and/or achieving or experiencing a more pleasurable orgasm. In particular, the inventor has found that providing acoustic wave therapy is beneficial in aiding with these issues as a starting point. In another aspect, the inventor has found that combining the acoustic wave therapy with one or more of providing suction stimuli and vibration stimuli in a single session is further beneficial in enhancing female arousal, sexual pleasure and/or achieving or experiencing a more pleasurable orgasm. To the best of the inventor's knowledge, acoustic wave therapy has not been used in combination with at least one of suction therapy and vibration therapy using certain protocols, in accordance with the teachings herein, to enhance female arousal, sexual pleasure and/or achieving or experiencing a more pleasurable orgasm. The various embodiments described herein relate to use of a device and methods for providing the stimuli described herein.

Acoustic wave therapy, which may also be known as shock wave therapy depending on the characteristics of the acoustic waves (i.e. intensity, rise time, time duration and frequency), typically involves the use of sound waves to reduce various conditions such as muscle pain, joint pain, back pain, ischemia, plantar fasciitis, Achilles tendinopathy, patellar tendinopathy, and erectile dysfunction and dementia. Acoustic wave therapy is generally known for providing pain relief and improving mobility. The sound waves are generated with a certain intensity, frequency range and time duration. The sound waves are provided as repeated pulses of high energy to certain areas on a person using a probe or an applicator. The acoustic energy helps to repair and regenerate tissue, tendons and bones.

Suction therapy, which is also known as cupping therapy, involves applying suction to a person's skin. The suction may be applied by using cups that are made of glass, plastic or another suitable material. The suction may be used to help with reducing pain, reducing inflammation, increasing blood flow and/or improving relaxation. A pump may be coupled to the cup via a tube so that the pump can remove air from the cup after the cup has been applied to a person's skin thereby creating a negative pressure within the cup which has the effect of applying a suction with a certain intensity. Alternatively, the interior of a cup may be heated and then placed on the skin and while the inside of the cup cools, there is a decrease in pressure which thereby provides suction.

Vibration therapy may involve whole body vibration in which a vibration stimulus is applied to a person's whole body and localized vibration therapy in which a vibrating device may be used to apply a vibration stimulus to certain parts of a person's body. Vibration therapy causes a person's muscles to contract and relax and may also cause the person's body to create increased levels of osteoblasts. The direction and intensity at which the vibrations are applied to the person's body may affect the benefit of vibration therapy on the person. Vibration therapy has been claimed to increase muscle mass and bone density, reduce pain and stress, and improve blood circulation and metabolism.

Reference is now made to FIG. 1, which illustrates an example embodiment of a device 100 that may be used for performing at least one of improving or enhancing female sexual arousal, sexual pleasure and/or achieving or experiencing a more pleasurable orgasm in accordance with the teachings herein. The term "female sexual function" is meant to encompass female sexual arousal, female sexual pleasure and/or achieving or experiencing a more pleasurable orgasm for the female. The improvement in female sexual function described herein can also include increased lubrication during arousal and intercourse.

The device 100 comprises a power switch 102, a power module 103, a control unit 104, a user interface 105, an acoustic unit 106, and a memory unit 107. The device 100 is provided as an example and there may be other embodiments of the device 100 with different components or a different configuration of the components described herein. For example, the device 100 may include other elements that can be used for operation as is understood by those skilled in the art.

In general, the user interface 105 is used to set values for stimulus parameters. The acoustic unit 106 is configured to provide an acoustic stimulus at the female perineum. The female perineum is the area between the vulva and the anus and includes the clitoral region and the perineal region (also known as the perineal body). The clitoral region includes the clitoris and some surrounding structures such as the frenulum of clitoris, and the glans of clitoris, the labium majus and the labium minus. The female perineum also includes the muscles and neurovasculature of the associated urogenital structures.

The control unit 104 controls the operation of the device 100 and can include any suitable processor, controller or digital signal processor that can provide sufficient processing power as is known by those skilled in the art. For example, the control unit 104 may include a high performance processor. In alternative embodiments, the control unit 104 may include more than one processor with each processor being configured to perform different dedicated tasks. In alternative embodiments, specialized hardware can be used to provide some of the functions provided by the control unit 104.

The power module 103 can be any suitable power source that provides power to the various components of the device unit 100. For example, the power module 103 may be a power supply or a power adaptor that is connected to a power source through a power outlet, for example. Alternatively, the power module 103 may be a rechargeable battery pack depending on the implementation of the device 100 as is known by those skilled in the art. The power switch 102 is coupled to the power module 103 and may be a button, switch, a slider or any other input element that a user may adjust to turn on the device 100 and then turn off the device 100 when it is no longer needed.

The memory unit 107 can include RAM, ROM, one or more hard drives, one or more flash drives or some other suitable data storage elements. The memory unit 109 may be used to store an operating system and programs that are used to operate the device 100 as is commonly known by those skilled in the art. For instance, the operating system provides various basic operational processes for the device 100 and the programs include a user program that a user can interact with to control the acoustic unit 106. The memory unit 107 may also be used to store data for the device 100 such as system settings, parameter values, calibration data and user data.

A user uses the user interface 105 to input control data to control the device 100 and set stimulus parameters to control various parameters of the acoustic stimulus, such as stimulus intensity, stimulus frequency and stimulus duration. The user interface 105 provides the control data to the control unit 104 which then controls the acoustic unit 106 to produce the acoustic stimulus, respectively, according to the stimulus parameters.

The user interface 105 can include at least one of a mouse, a keyboard, a touch screen, a thumbwheel, a track-pad, a track-ball, a card-reader, voice recognition software and the like again depending on the particular implementation of the device 100. In some cases, some of these components can be integrated with one another. The user interface 105 may also include a display that provides visual information regarding the operation of the device 100 and the provision of the various stimuli such as showing the stimulus parameters, the time duration of stimulus application and the like. The user interface 105 may also include I/O hardware (not shown) which can include, but is not limited to, at least one of a microphone, a speaker, and a printer, for example.

The device 100 may also include other units such as a communication unit (not shown) that allows the device 100 to communicate with other devices. For example, the communication unit may include a radio for wireless communication that can communicate using CDMA, GSM, GPRS or Bluetooth protocol according to standards such as IEEE 802.11a, 802.11b, 802.11g, or 802.11n. Alternatively, or in addition thereto, the device 100 may include a communication port (not shown) such as a parallel port, a serial port or a USB port that and/or communication busses such as at least one of a SCSI, USB, IEEE 1394 interface (FireWire), Parallel ATA, Serial ATA, or PCIe. These busses and/or ports may be used to connect the device 100 to the Internet, a Local Area Network (LAN), a Wide Area Network (WAN), a Metropolitan Area Network (MAN), a Wireless Local Area Network (WLAN), a Virtual Private Network (VPN), or a peer-to-peer network, either directly or through a modem, router, switch, hub or other routing or translation device. These various communication elements allow the device 100 to send and/or receive information across a network connection to a remote system.

The acoustic unit 106 includes various components that are used to create the acoustic stimulus. For example, the acoustic unit 106 can include an acoustic signal generator, an amplifier, a filter and an acoustic probe 106*p* with an acoustic transducer to provide acoustic energy. The control unit 104 provides acoustic control signals to the acoustic signal generator so that the appropriate amount of acoustic energy is provided by the acoustic probe 106*p* to certain regions of the female genitalia including at least one of the female's clitoral region and the perineum. Furthermore, more or less acoustic energy can be applied according to the comfort level of the patient through computer controlled regulation of the device 100. In addition, a particular type of acoustic energy can be provided, i.e. one of the acoustic shockwave signals or a pressure wave, based on the effectiveness of the acoustic signal with the particular female who receives the acoustic stimulus. For example, while acoustic shockwaves may be used, the inventor has discovered that acoustic pressure waves may in general be more effective at improving or enhancing female sexual arousal, sexual pressure and/or ability to achieve or experience a more pleasurable orgasm. The acoustic probe 106*p* can have a plastic, silicone, gel, ceramic or steel head that can be 15 mm or 20 mm in diameter. In some embodiments, the amount of acoustic energy may be varied between various intensity levels from 0.08 to 0.47 $mJ/mm^2$ and can also be affected by using certain applicators and the amount/quality of coupling between the applicator and the perineum.

Figure 2:
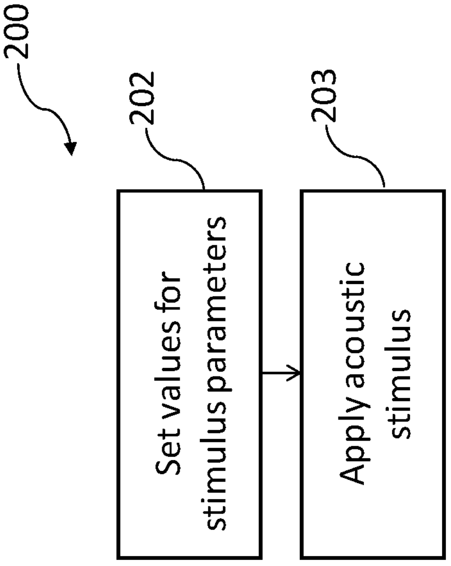
FIG. 2 is a flowchart of an example embodiment of a method for enhancing female arousal, sexual pleasure and/or achieving or experiencing a more pleasurable orgasm comprising applying an acoustic stimulus in accordance with the teachings herein.

Reference is now made to FIG. 2, which illustrates a flowchart of an example embodiment of a method 200 for performing at least one of enhancing or improving female sexual arousal, sexual pressure and/or ability to achieve or experience a more pleasurable female orgasm in accordance with the teachings herein.

At act 202 of method 200, values are set for the stimulus parameters for the acoustic stimulus that will be provided to the female. For example, for the acoustic stimulus, the stimulus parameters that may be set include an intensity level, a frequency range, a pulse repetition rate, a rise time, a fall time and a time duration for generating the acoustic stimulus.

At act 203 of method 200, the acoustic stimulus is applied at the perineum of the female. More particularly, the acoustic stimulus may be applied to the clitoral region or the perineal body, both the clitoral region and the perineal body of the perineum or possibly other structures at the perineum. When the acoustic stimulus is applied to both the clitoral region and the perineal body, it may be applied in either order. In some embodiments, a gel may be applied to a region of the female prior to providing the acoustic stimulus to the region. The gel provides a better coupling between the physical surfaces of the acoustic probe 106*p* and the region that receives the stimulus which reduces any degradation of the acoustic stimulus due to a mismatch in acoustic impedance between the acoustic probe 106*p* and the region of the female that receives the stimulus. The gel may be any type of ultrasound coupling gel. In some cases, the gel may be a freezing or numbing gel.

The user activates the acoustic unit 106 and then positions the acoustic probe 106*p* against the region that is to receive the acoustic stimulus (e.g. the clitoral region, the perineal body and/or other nearby structures). For example, the user may apply the acoustic probe against the clitoral region for about 1000 pulses, or against the perineal body for about 1000 pulses or against both the clitoral region and the perineal body for about 1000 pulses each in any order. In alternative embodiments, the number of pulses can range from 500 to 3000 pulses for one or more of the clitoral region and perineal body. In some cases, the acoustic stimulus may be applied with an intensity in between about 0.08 to 0.47 mJ/mm$^2$, and more preferably between 0.1 and 0.47 mJ/mm$^2$. In some cases, the acoustic stimulus may have a frequency range from about 4 to 15 Hz. In some cases, the acoustic stimulus may be have a frequency of about 11 Hz. In some cases, the acoustic stimulus may be applied for about 1 to 10 minutes and more preferably from about 2 to 4 minutes depending on the amount of stimulus that the female needs to receive an improvement in female sexual function. In some cases, the amount of acoustic energy is selected to be between about 1.0 to 3.6 bars when the device 100 is the MASTERPULS® "ULTRA" MP200 along with one of the acoustic probes that can be used with this device. The user then removes the acoustic probe 106*p* and deactivates the acoustic unit 106. The energy associated with these bar settings for these devices which use an acoustic probe 106*p* having a transducer that is about 15 mm in diameter is shown in Table 1. This acoustic probe is the R15 Storz acoustic probe. From Table 1 it can be seen that the relation between bars and EFD is somewhat linear while the relation between bars and output pressure are nonlinearly related and can be interpolated using a nonlinear function that fits the data points in Table 1. The energy values for the settings when using other acoustic probes may be obtained from the equipment manufacturer.

TABLE 1

Intensity values for the ultrasonic component of acoustic waves generated by an acoustic probe with a 15 mm transducer

| | Driving Pressure [bar] | | | | |
|---|---|---|---|---|---|
| | 1 | 2 | 3 | 4 | 5 |
| EFD [mJ/mm$^2$] | 0.05 | 0.11 | 0.17 | 0.22 | 0.28 |
| Output Pressure [MPa] | 2.2 | 5.2 | 9.5 | 14.3 | 19.7 |

Figure 3:
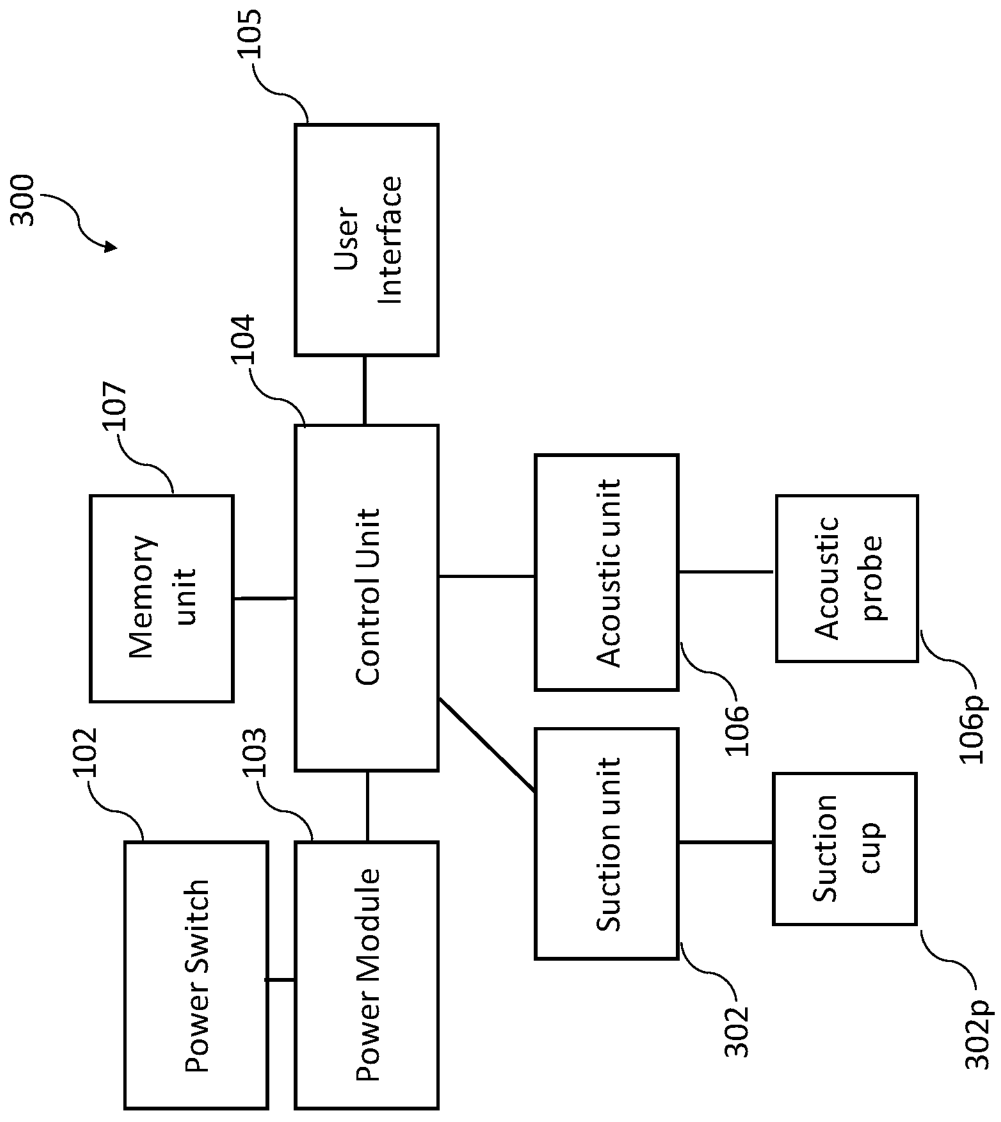
FIG. 3 is a block diagram of an example alternative embodiment of a device capable of producing acoustic and suction stimuli that may be used to perform one or more of the various methods described in accordance with the teachings herein.

Reference is now made to FIG. 3, which illustrates an example embodiment of a device 300 that may be used for performing at least one of enhancing or improving female sexual arousal, sexual pressure and/or ability to achieve or experience a more pleasurable orgasm in accordance with the teachings herein. The device 300 comprises the components of device 100, which operate similarly for device 300. The device 300 further comprises a suction unit 302 that is configured to provide a suction stimulus at the perineum. The device 300 is provided as an example and there may be other embodiments of the device 300 with different components or a different configuration of components.

The suction unit 302 includes various components that are used to create the suction stimulus. For example, the suction unit 302 can include a suction circuit driver and a pump (both not shown), and the device 300 generally includes a suction cup 302*p*. The control unit 104 provides suction control signals to the circuit driver to operate the pump so that the appropriate amount of suction is provided by the suction cup 302*p* when the suction cup 302*p* is applied to the female's clitoral region. Furthermore, more or less suction can be applied according to the comfort level of the patient through computer controlled regulation of the device 300. The suction cup 302*p* can be made of glass or plastic and may come in various sizes such as 25 mm, 33 mm, 47 mm, and 62 mm in diameter. The amount of suction may be varied by setting levels between about 1 to 5 bars when the device 300 is the MASTERPULS® "ULTRA" MP200 and the VACU-ACTOR® accessory is the suction probe 302*p*. The values for the suction stimulus based on these settings are shown in the tables below for providing the suction stimulus intermittently (see Table 2) or continuously (see Table 3).

TABLE 2

Suction Intensity level for intermittent underpressure/vacuum (mbar) estimated

| | Intensity level (Bars)| | | | | |
|---|---|---|---|---|---|
| Frequency (Hz) | 1 | 2 | 3 | 4 | 5 |
| 2 | −40 | −80 | −130 | −150 | −200 |
| 3 | −30 | −70 | −100 | −120 | −160 |
| 4 | −30 | −60 | −80 | −100 | −140 |
| 5 | −20 | −50 | −70 | −90 | −130 |

TABLE 3

Suction Intensity level for continuous underpressure/vacuum (mbar)

| | Intensity level (Bars) | | | | |
|---|---|---|---|---|---|
| Frequency [Hz] | 1 | 2 | 3 | 4 | 5 |
| 2 | −200 | −260 | −300 | −400 | −470 |
| 3 | −200 | −270 | −300 | −400 | −470 |
| 4 | −200 | −270 | −300 | −400 | −470 |
| 5 | −210 | −260 | −300 | −380 | −450 |

In this example embodiment, the user operates the user interface 105 to input control data to control the device 300 and set stimulus parameters to also control various parameters of the suction stimulus such as stimulus intensity (i.e. amount of suction), whether the suction is provided continuously or intermittently and the stimulus duration. The user interface 105 provides the control data to the control unit 104 which then controls the suction unit 302 and the acoustic unit 106 to produce the suction stimulus and acoustic stimulus, respectively, according to the stimulus parameters.

Figure 4:
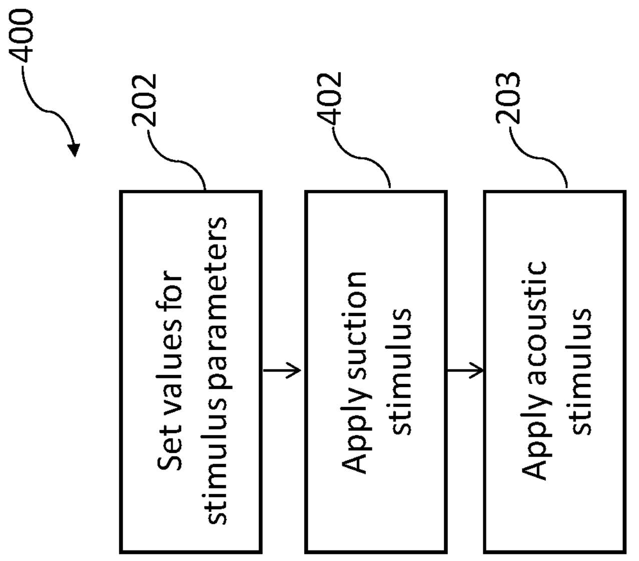
FIG. 4 is a flowchart of an example alternative embodiment of a method for enhancing female arousal, sexual pleasure and/or achieving or experiencing a more pleasurable orgasm comprising applying an acoustic and suction stimulus in accordance with the teachings herein.

Reference is now made to FIG. 4, which illustrates a flowchart of an example embodiment of a method 400 for performing at least one of enhancing or improving female sexual arousal, sexual pressure and/or ability to achieve or experience a more pleasurable orgasm in accordance with the teachings herein.

At act 202 of method 400, values are set for the stimulus parameters for the various stimuli that will be provided to the female. For example, for the suction stimulus, the stimulus parameters that may be set include a suction intensity level, whether the suction is generated consistently or intermittently and the time duration for generating the suction stimulus. For the acoustic stimulus, the stimulus parameters may be set as described in method 200.

At act 402 of method 400, the suction stimulus is applied at the perineum of the female and more particularly to the clitoral region of the perineum. The user activates the suction unit 302 and then positions the suction cup 302*p* against the skin around the clitoral region of the female for a desired period of time. The suction cup 302*p* can have a certain size as described previously. The suction stimulus can be applied with an intensity of about 1 to 5 bars as described previously. The level of 5 bars provides the most negative pressure in the suction cup 302*p*. In at least some cases, the level may be preferably set to 3 bars. In some cases, the suction stimulus can be applied for about 1 to 4 minutes. For example, the suction stimulus can be preferably applied for about 2 to 3 minutes. The user then removes the suction cup 302*p* and deactivates the suction unit 302. Alternatively, the user may use a separate cup, heat it and apply it to the female as described previously. With the VACU-ACTOR accessory, the suction can be set to intermittent or continuous mode and in at least some cases it is preferably set to continuous. When it is set to intermittent mode the frequency can vary between 1 and 5 Hz and it is preferably set to about 3 Hz.

At act 203 of method 400, the acoustic stimulus is applied as explained for method 200.

It should be noted that with method 400, the suction stimulus and the acoustic stimulus are provided in a single session. There may be a wait time from about 0 to 3 minutes and more preferably 0 to 2 minutes after the first stimulus type (i.e. suction) is applied before the next stimulus type (i.e. acoustic) is applied. Several sessions may be provided to the female spaced several days apart. Furthermore, it should be noted that there can be an alternative embodiment in which the acoustic stimulus is provided before the suction stimulus. However, the inventor has found that providing the suction stimulus before the acoustic stimulus may provide better results since the suction stimulus can be used to draw more blood to the female's clitoris and/or perineum allowing the acoustic stimulus which is applied next to be more effective in improving or enhancing the sexual arousal, sexual pleasure and/or the ability to achieve or experience a more pleasurable orgasm for the female who receives these stimuli.

Figure 5:
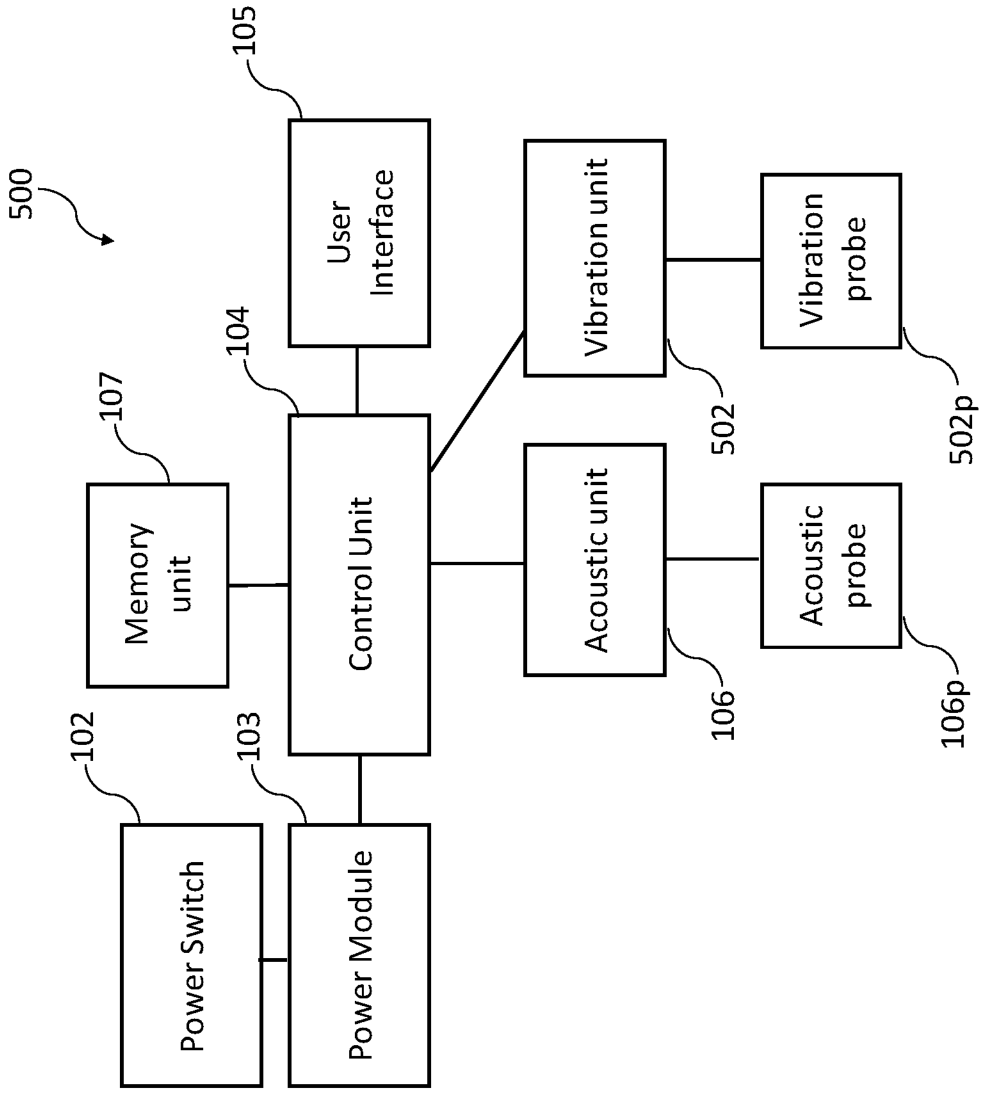
FIG. 5 is a block diagram of an example alternative embodiment of a device capable of producing acoustic and vibration stimuli that may be used to perform one or more of the various methods described in accordance with the teachings herein.

Reference is now made to FIG. 5, which illustrates an example embodiment of a device 500 that may be used for performing at least one of enhancing female sexual arousal, sexual pressure and/or ability to achieve or experience a more pleasurable orgasm in accordance with the teachings herein. The device 500 comprises the components of device 100, and further comprises a vibration unit 502. The device 500 is provided as an example and there may be other embodiments of the device 500 with different components or a different configuration of the components.

The vibration unit 502 includes various components that are used to create the vibration stimulus. For example, the vibration unit 502 can include a vibration signal generator, an amplifier (both not shown), and a vibration probe 502*p* having a mechanical transducer to provide the vibration stimulus. The control unit 104 provides vibration control signals to the vibration signal generator so that the appropriate amount of a vibration stimulus having an appropriate amount of vibrational energy is provided by the vibration probe 502*p* to the female's clitoral region. Furthermore, more or less vibrational energy can be applied according to the comfort level of the patient through computer controlled regulation of the device 500. The vibration probe 502*p* has a vibration head that may come in different sizes, such as, but not limited to, having an outer diameter of 10 mm, 20 mm, 25 mm, and 40 mm, depending on the size of the clitoral region of the female who receives the vibration stimulus. The amount of vibrational energy may be varied to provide a displacement in the vibration stimulus with an amplitude of 1 to 4 mm and energy levels from about 0.08 to 0.3 $mJ/mm^2$ depending on the intensity level of the vibration stimulus and the size of the vibration probe 502*p*. The frequency range of the vibration stimulus is from 0 Hz to 31 Hz. In some cases, the amount of vibrational energy is selected to be between about 1.6 to 2.8 bars when the device 500 is the MASTERPULS® "ULTRA" MP200 and the V-ACTOR® accessory is the vibration probe 502*p*.

As with device 100, the user interface 105 is used to set values for stimulus parameters. The vibration unit 502 is configured to provide a vibration stimulus at the perineum, and the acoustic unit 106 is configured to provide an acoustic stimulus at the perineum. The user operates the user interface 105 to input control data to control the device 500 and set stimulus parameters to control various parameters of the vibration stimulus, and the acoustic stimulus such as stimulus intensity, stimulus frequency and stimulus duration. The user interface 105 provides the control data to the control unit 104 which then controls the vibration unit 502 and the acoustic unit 106 to produce the vibration stimulus and acoustic stimulus, respectively, according to the stimulus parameters.

Figure 6:
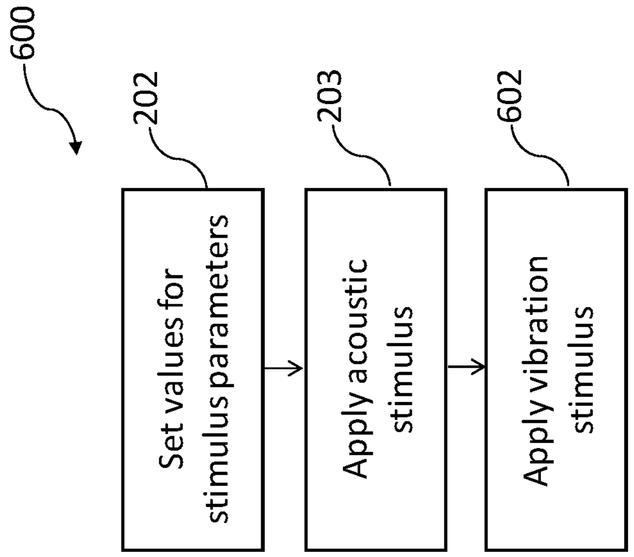
FIG. 6 is a flowchart of an example alternative embodiment of a method for enhancing female arousal, sexual pleasure and/or achieving or experiencing a more pleasurable orgasm comprising applying an acoustic and a vibration stimulus in accordance with the teachings herein.

Reference is now made to FIG. 6, which illustrates a flowchart of an example embodiment of a method 600 for performing at least one of enhancing or improving female sexual arousal, sexual pressure and/or ability to achieve or experience a more pleasurable orgasm in accordance with the teachings herein. For example, the female sexual condition may be at least one of female sexual arousal disorder, female orgasmic disorder, and female sexual pain disorder.

At act 202 of method 600, values are set for the stimulus parameters for the various stimuli that will be provided to the female. For the acoustic stimulus, the stimulus parameters may be set as described in method 200. For the vibration stimulus, the stimulus parameters that may be set include an intensity level, a pulse repetition rate and a time duration for generating the vibration stimulus.

At act 203 of method 600, the acoustic stimulus is applied at the perineum as described for method 200.

At act 602 of method 600, the vibration stimulus is applied at the perineum of the female and more particularly to the clitoral region of the female. In some embodiments, a gel may be applied to a region of the female prior to providing the vibration stimulus to the region. The gel provides a better coupling between the physical surfaces of the vibration probe 502*p* and the female's region receiving the acoustic stimulus and also helps to reduce friction there between. This coupling gel therefore reduces discomfort or chaffing of the female's region when it receives the vibration stimulus from the vibration probe 502*p*. The gel may be any type of suitable medical grade gel including, but not limited to, ultrasound coupling gel.

The user activates the vibration unit 502 and then positions the vibration probe 502*p* against the clitoral region of the female for a desired period of time. The vibration probe 502*p* can have a certain size as described previously. When the MASTERPULS® "ULTRA" MP200 is used along with the V-ACTOR® vibration probe, the vibration stimulus can be applied with an intensity of about 1.6 to 2.8 bars as described previously. In some cases, the vibration intensity can be at a level of 2.4 bars. As shown in Table 4, the bar values for the V-ACTOR® vibration probe have corresponding values for at least one of energy, energy flux density, displacement, and force. Also, in some cases, the vibration stimulus can have a frequency of about 21 Hz. In some cases, the vibration stimulus can be applied for about 30 seconds to 1 minute. For example, the vibration stimulus can be applied for about 1 minute. The user then removes the vibration probe 502*p* and deactivates the vibration unit 502.

TABLE 4

| Vibration intensity levels | | | | |
|---|---|---|---|---|
| Pressure input | Probe size (mm) | | | |
| (bars) | 10 | 25 | 40 | Units |
| 1.4 | | 0.7 | | mm (displacement) |
| 2 | | 2.2 | | mm (displacement) |
| 3 | | 3.2 | | mm (displacement) |
| 4 | 113 | 113 | 137 | mJ (energy) |
| | 0.9 | 0.2 | 0.1 | mJ/mm$^2$ (energy flux density) |
| | 21.3 | 11.3 | 14.5 | N (force) |
| | | 3.8 | | mm (displacement) |
| 5 | 137.6 | 136.6 | 166.3 | mJ (energy) |
| | 1.1 | 0.1 | 0.1 | mJ/mm$^2$ (energy flux density) |
| | 26.7 | 17.8 | 17.8 | N (force) |
| | | 4.08 | | mm (displacement) |

It should be noted that with method 600, the acoustic stimulus and the vibration stimulus are provided in a single session. There may be a wait time from about 0 to 3 minutes and more preferably 0 to 2 minutes after the first stimulus type (i.e. acoustic) is applied before the next stimulus type (i.e. vibration) is applied. Several sessions may be provided to the female spaced several days apart. Furthermore, it should be noted that there can be an alternative embodiment in which the vibration stimulus is provided before the acoustic stimulus. However, the inventor has found that providing the vibration stimulus after the acoustic stimulus may provide better results since the acoustic stimulus can be used to more vigorously excite the clitoris and/or perineum of the female to improve the amount of sensation felt by the female receive the stimulus while the vibration stimulus may be used to allow the clitoris and/or perineum of the female to more gradually return to a relaxed state helping to smooth the tissue that received the acoustic stimulus and improving the recovery time of the tissue from the application of the acoustic stimulus. Therefore, these two stimuli applied together in this manner appear to be more effective in improving or enhancing the sexual arousal, sexual pleasure and/or the ability to achieve or experience a more pleasurable orgasm for the female who receives these stimuli.

Figure 7:
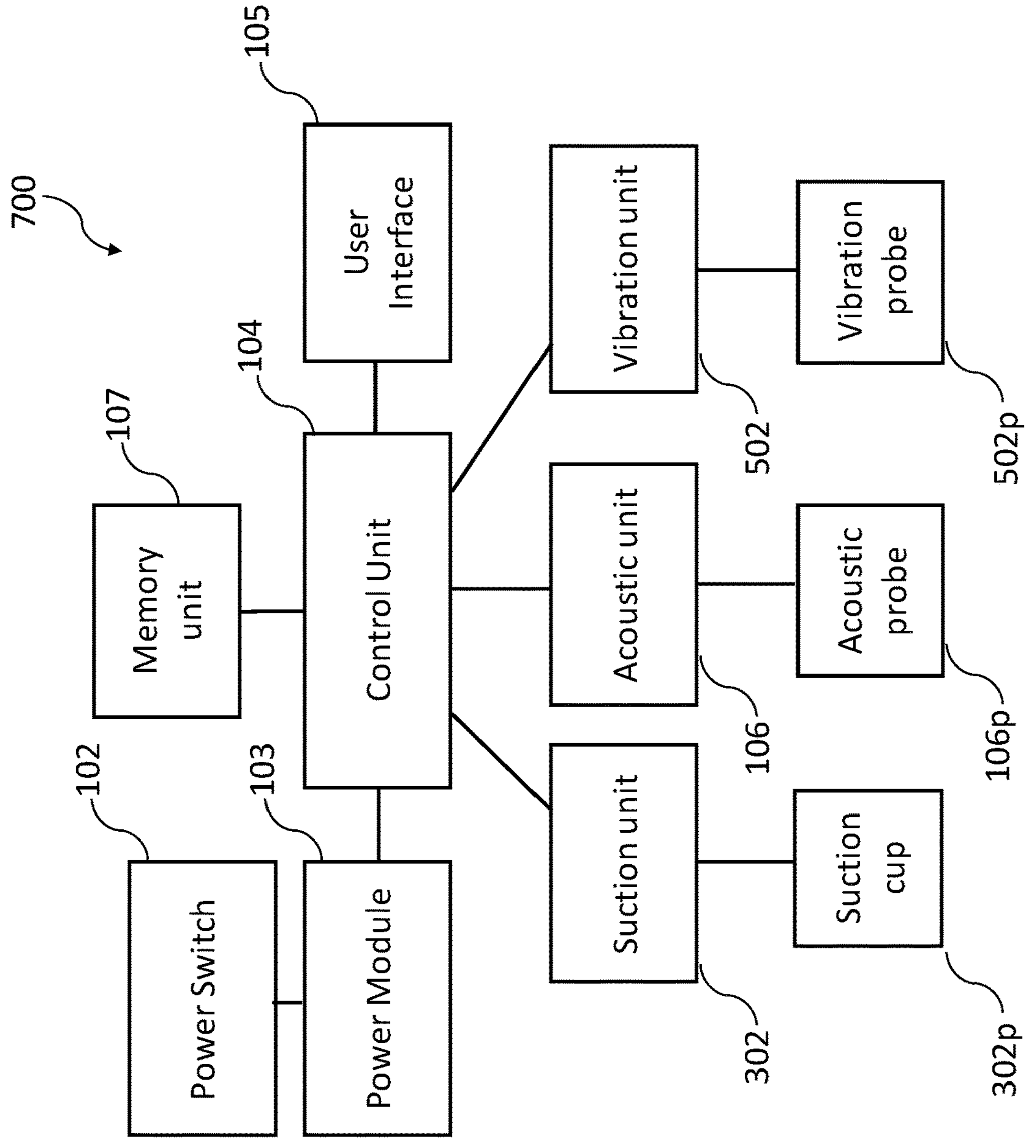
FIG. 7 is a block diagram of an example embodiment of a device capable of producing acoustic, suction, and vibration stimuli that may be used to perform one or more of the various methods described in accordance with the teachings herein.

Reference is now made to FIG. 7, which illustrates an example embodiment of a device 700 that may be used for performing at least one of enhancing or improving female sexual arousal, sexual pressure and/or ability to achieve or experience a more pleasurable orgasm in accordance with the teachings herein. The device 700 comprises the components of device 100, the suction unit 302 and suction cup 302*p* of device 300, and the vibration unit 502 and vibration probe 502*p* of device 500. The device 700 is provided as an example and there may be other embodiments of the device 700 with different components or a different configuration of the components.

As with device 100, the user interface 105 is used to set values for stimulus parameters. The suction unit 302 is configured to provide a suction stimulus at the perineum, the acoustic unit 106 is configured to provide an acoustic stimulus at the perineum, and the vibration unit 502 is used to provide a vibration stimulus at the perineum.

The user operates the user interface 105 to input control data to control the device 300 and set stimulus parameters to control various parameters of the suction stimulus, the vibration stimulus and the acoustic stimulus, such as stimulus intensity, stimulus frequency, stimulus duration, and in some cases the rise time and the fall time for the acoustic stimulus. The user interface 105 provides the control data to the control unit 104 which then controls the suction unit 302, the acoustic unit 106 and the vibration unit 502 to produce the suction stimulus, the acoustic stimulus, and the vibration stimulus, respectively, according to the stimulus parameters.

It should be noted that in at least some embodiments, the device 700 can be provided by a commercial device such as the MASTERPULS® "ULTRA" MP200 along with the V-ACTOR® and the VACU-ACTOR accessories, which are provided by SHOCKWAVE Canada Inc. Alternatively, a collection of commercial devices may be used together to provide the suction stimulus, vibrator stimulus and acoustic wave therapy. In some cases, a separate cup can be heated and applied to the female may be used.

Figure 8:
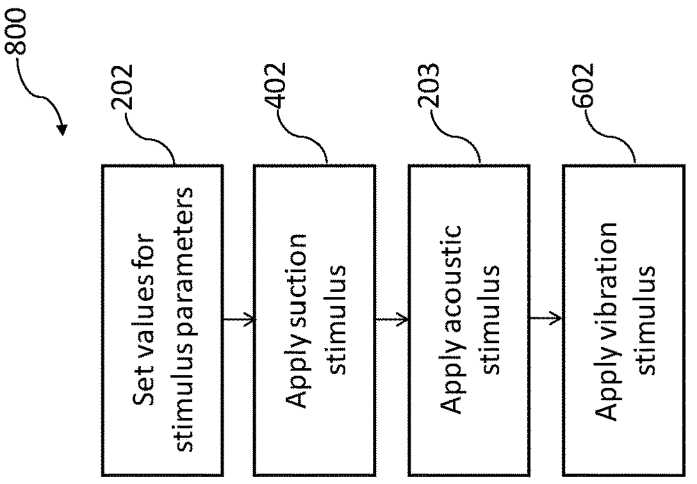
FIG. 8 is a flowchart of an example embodiment of a method for enhancing female arousal, sexual pleasure and/or achieving or experiencing a more pleasurable orgasm comprising applying a suction, an acoustic, and a vibration stimulus in accordance with the teachings herein.

Reference is now made to FIG. 8, which illustrates a flowchart of an example embodiment of a method 800 for performing at least one of enhancing or improving at least one or female sexual arousal, sexual pressure and/or ability to achieve or experience a more pleasurable orgasm in accordance with the teachings herein.

At act 202 of method 800, values are set for the stimulus parameters for the various stimuli that will be provided to the female. For example, for the suction stimulus, the acoustic stimulus, and the vibration stimulus may be set as described in methods 200, 400 and 600. Method 800 then comprises performing acts 402, 203, and 602 in which the suction stimulus, the acoustic stimulus, and the vibration stimulus are applied as described previously.

It should be noted that when the three stimuli are provided in the order of providing the suction stimulus, then the acoustic stimulus and then the vibration stimulus, the greatest improvement or enhancement in female sexual function was observed by the inventor. As described previously, applying the suction stimuli first drives more blood flow to the region that then receives the acoustic stimuli which makes the acoustic stimuli more effective. Thereafter, the application of the vibration stimulus helps the region that receives the suction and acoustic wave stimuli to recover and repair faster and more effectively. There may be a wait time from about 0 to 3 minutes and more preferably 0 to 2 minutes after the first stimulus type (i.e. suction) is applied before the next stimulus type (i.e. acoustic) is applied.

The methods 200, 400, 600, and 800 may be performed using the devices 100, 300, 500, 700, or devices such as the MASTERPULS® "ULTRA" MP200 along with the V-ACTOR® and the VACU-ACTOR accessories or alternative devices that provide the functionality and stimulus ranges described herein.

In some embodiments, the methods 200, 400, 600, and 800 can be performed two to three times per week at an interval of two to 3 days (i.e. a rest period in between successive sessions (i.e. applications of the methods) to a female).

In some embodiments, the number of sessions may range from about two to 12 sessions depending on how sensitive the female is to receiving these stimuli.

In some embodiments, a session in which one, two or three different types of stimuli are applied can range from about two to 10 minutes.

In some embodiments, it may be possible to change the order of applying the various stimuli from what is shown in FIGS. 4, 6, and 8 because a given order of stimuli may still provide at least some benefit for a female. For example, in some embodiments for methods 600 and 800, the user may apply the vibration stimulus first followed by the acoustic stimulus, the suction stimulus or the acoustic and suction stimuli (in either order). Alternatively, in some embodiments for methods 400 and 800, the user may apply the acoustic stimulus first followed by the suction stimulus, the vibration stimulus or the suction and vibrations stimuli (in either order).

EXAMPLE

Study Objectives:

Pain, adverse events, and quality of sexual satisfaction was studied before and after applying acoustic wave, suction and vibration stimuli.

Population:

Five women between the ages of 29 and 60 were included in the study. One patient had a neurologic deficit in the S1 distribution and thus had decreased sensation in the clitoral area. One woman had two children, and the other three did not have any children or medical conditions.

Intervention:

Four sessions were performed twice per week, three days apart on the five women. Each session comprised application of a suction cup or cupping device for approximately two to three minutes, followed by one thousand to two thousand radial shockwaves at a setting of about 1.8 to 2.6, followed by application of a vibration stimulus at a frequency of about 21 Hz for about 1 to 2 min using the MASTERPULS® "ULTRA" MP200 along with the V-ACTOR® and the VACU-ACTOR accessories. Ranges have been specified since the stimuli were varied according to the tolerance level of the woman who was receiving the stimuli.

Results:

All of the women described enhanced orgasm, more pleasurable orgasms and one woman was able to achieve multiple orgasms which she never had been able to do prior to the sessions. The woman with neurologic deficiency also experienced enhanced pleasure and lubrication and satisfaction with sexual intercourse. Following the sessions some women described increased sexual desire, increased arousal during intercourse, and were very satisfied with their arousal during sexual activity and intercourse. Furthermore, all five women described an enhancement/improvement of orgasm.

Various embodiments of devices and methods have been described herein by way of example only. Furthermore, the methods described herein may be used for the enhancing or improving female sexual function including at least one of female sexual arousal, female sexual pleasure, achieving or experiencing a more pleasurable orgasm for the female. Various modifications and variations may be made to these example embodiments without departing from the spirit and scope of the embodiments, which is limited only by the appended claims which should be given the broadest interpretation consistent with the description as a whole.

REFERENCES

Berman, J R., Goldstein, I., *Female sexual dysfunction, Urologic Clinics*, Volume 28, Number 2, pp. 405-16, May 2001.

Meston, C M., Hull, E., Levin R J., Sipski, M., *Disorders of orgasm in women*, The Journal of Sexual Medicine, Volume 1, Issue 1, pp. 66-68, July 2004.

The invention claimed is:

1. A method for performing at least one of enhancing female sexual arousal, enhancing female sexual pleasure, and/or enhancing an ability to achieve or experience a more pleasurable orgasm for a female, wherein the method comprises:

setting values for stimulus parameters;

applying a suction stimulus to the perineum of the female;

applying an acoustic stimulus at the perineum of the female after applying the suction stimulus, wherein the acoustic stimulus comprises shockwaves; and applying a vibrational stimulus to the perineum of the female after applying the acoustic stimulus, wherein the stimuli are applied one at a time in the same session.

2. The method of claim 1, wherein the method comprises applying the acoustic stimulus to at least one of a clitoral region and a perineal body of the perineum in any order.

3. The method of claim 2, wherein the method comprises applying at least one of about 500 to 2000 acoustic pulses to the clitoral region and about 500 to 2000 acoustic pulses to the perineal body.

4. The method of claim 2, wherein the method comprises applying the acoustic stimulus with an intensity of about 0.1 to 0.25 $mJ/mm^2$.

5. The method of claim 2, wherein the method comprises applying the acoustic stimulus at a frequency of about 4 to 15 Hz.

6. The method of claim 2, wherein the acoustic stimulus comprises low energy shockwaves, pressure pulses, or radial shockwaves.

7. The method of claim 2, wherein the method comprises applying the acoustic stimulus for about 2 to 4 minutes.

8. The method of claim 1, wherein the method comprises continuously applying the suction stimulus to a clitoral region of the perineum with an intensity of about 200 to 470 mbar at a frequency of about 1 to 5 Hz using a device comprising:

a user interface that is configured to set the values for the stimulus parameters;

an acoustic unit comprising an acoustic probe that is configured to provide the acoustic stimulus to the perineum of the female;

a suction unit comprising a suction probe that is configured to provide the suction stimulus to the perineum of the female; and a vibration unit comprising a vibration probe that is configured to provide the vibration stimulus to the perineum of the female, wherein the suction probe comprises a cup ranging from about 20 to 65 mm in diameter.

9. The method of claim 1, wherein the method comprises applying the suction stimulus for about 1 to 4 minutes.

10. The method of claim 1, wherein the method comprises applying the vibration stimulus to a clitoral region with a frequency of about 1 to 35 Hz and a displacement of about 0.7 to 3.2 mm using a device comprising:

a user interface that is configured to set the values for the stimulus parameters;

an acoustic unit comprising an acoustic probe that is configured to provide the acoustic stimulus to the perineum of the female;

a vibration unit comprising a vibration probe that is configured to provide the vibration stimulus to the perineum of the female; and a suction unit comprising a suction probe that is configured to provide the suction stimulus to the perineum of the female, wherein the vibration probe comprises a head ranging from about 10 to 40 mm in diameter.

11. The method of claim 1, wherein the method comprises applying the vibration stimulus with a frequency of about 21 Hz.

12. The method of claim 1, wherein the method comprises applying the vibration stimulus for about 30 seconds to 1 minute.

13. The method of claim 1, wherein the method is performed on the patient two to three times per week at an interval of two to three days.

14. Use of a device for performing at least one of enhancing female sexual arousal, enhancing female sexual pleasure, and/or enhancing an ability to achieve or experience a more pleasurable orgasm for a female, the device comprising:

a user interface that is configured to set values for stimulus parameters;

a suction unit that is configured to provide a suction stimulus at a perineum of the female;

an acoustic unit that is configured to provide an acoustic stimulus at the perineum of the female after the application of the suction stimulus, wherein the acoustic stimulus comprises shockwaves; and a vibration unit that is configured to provide a vibration stimulus to the perineum, wherein the use comprises:

using the user interface to set values for stimulus parameters;

using the suction unit to apply the suction stimulus at the perineum of the female;

using the acoustic unit to apply the acoustic stimulus at the perineum of the female; and using the vibration unit to apply the vibrational stimulus to the perineum of the female, wherein the stimuli are applied one at a time in the same session.

15. The use of claim 14, wherein the acoustic unit comprises an acoustic probe with a head ranging from about 15 to 35 mm in diameter that is configured to provide the acoustic stimulus and the use comprises applying the acoustic stimulus to at least one of a clitoral region and a perineal body of the perineum with an intensity in a range of about 0.1 to 0.25 $mJ/mm^2$ for about 2 to 3 minutes.

16. The use of claim 14, wherein the suction unit comprises a suction probe having a cup ranging from about 20 to 65 mm in diameter that is configured to provide the suction stimulus and the use comprises applying the suction stimulus to at least one of a clitoral region and a perineal body of the perineum with an intensity in a range of about 20 to 470 mbar for about 1 to 4 minutes.

17. The use of claim 14, wherein the vibration unit comprises a vibration probe with a head ranging from about 10 to 40 mm in diameter that is configured to provide the vibration stimulus and the use comprises applying the vibration stimulus to at least one of a clitoral region and a perineal body of the perineum with a frequency of about 1 to 35 Hz and a displacement of about 0.7 to 3.2 mm for about 30 seconds to 1 minute.

18. The method of claim 1, wherein the method comprises intermittently applying the suction stimulus to a clitoral region of the perineum with an intensity of about 20 to 200 mbar at a frequency of about 1 to 5 Hz using a device comprising:

a user interface that is configured to set the values for the stimulus parameters;

an acoustic unit comprising an acoustic probe that is configured to provide the acoustic stimulus to the perineum of the female;

a suction unit comprising a suction probe that is configured to provide the suction stimulus to the perineum of the female; and a vibration unit comprising a vibration probe that is configured to provide the vibration stimulus to the perineum of the female, wherein the suction probe comprises a cup ranging from about 20 to 65 mm in diameter.

* * * * *